Figure 3:
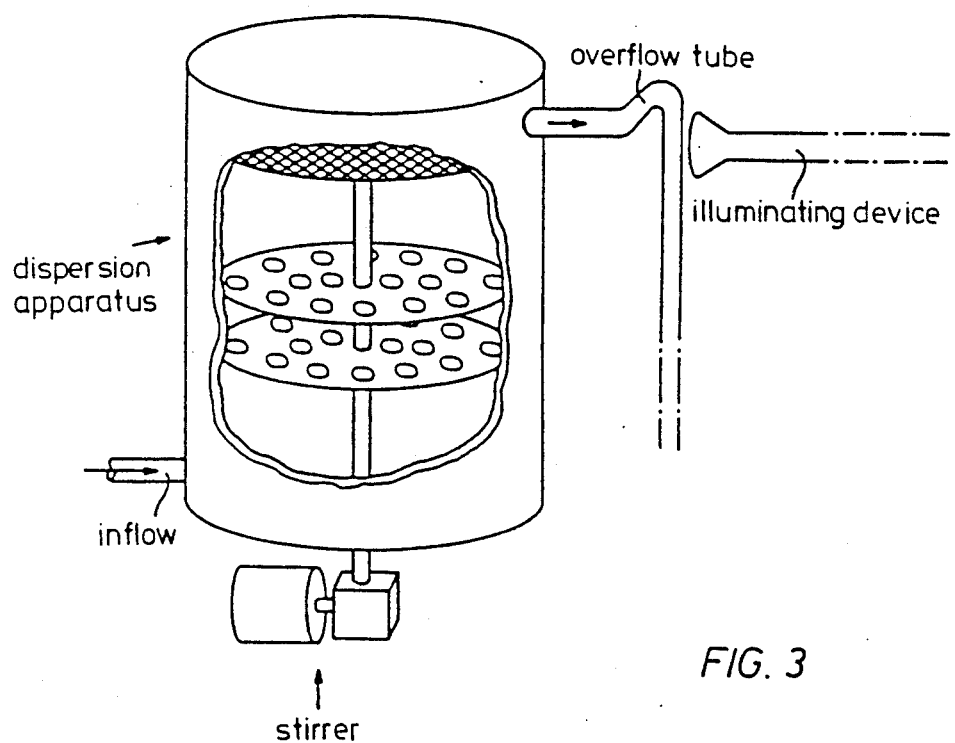

United States Patent [19]

Schulz

[11] Patent Number: 5,022,758

[45] Date of Patent: Jun. 11, 1991

[54] ARRANGEMENT FOR DETERMINING THE DEGREE OF DISPERSION OF MAGNETIC PIGMENTS IN A DISPERSION

[75] Inventor: Horst Schulz, Miesbach, Fed. Rep. of Germany

[73] Assignee: BASF Magnetics GmbH, Mannheim, Fed. Rep. of Germany

[21] Appl. No.: 242,521

[22] Filed: Sep. 12, 1988

[30] Foreign Application Priority Data

Sep. 22, 1987 [DE] Fed. Rep. of Germany ....... 3731804

[51] Int. Cl.[5] .................... G01N 15/02; G01N 21/85; G01N 21/49; G01B 5/842
[52] U.S. Cl. .................................................. 356/319
[58] Field of Search ...................... 356/319, 446, 323; 250/574

[56] References Cited

U.S. PATENT DOCUMENTS

| | | | |
|---|---|---|---|
| 3,601,589 | 8/1971 | McCarty | 356/402 |
| 4,449,821 | 5/1984 | Lee | 356/319 |
| 4,583,858 | 4/1986 | Lebling et al. | 356/446 |
| 4,756,619 | 7/1988 | Gerlinger et al. | 356/319 |
| 4,758,275 | 7/1988 | Yabakami et al. | 106/20 |

OTHER PUBLICATIONS

Diano Corporation, "Color Technology and Its Applications in Industry", Feb. 1970, p. 28.

Primary Examiner—Richard A. Rosenberger
Attorney, Agent, or Firm—Connolly and Hutz

[57] ABSTRACT

This invention relates to an arrangement for determining the degree of dispersion of magnetic pigments in a dispersion, in which the magnetic dispersion flowing along a transparent tube or a transparent wall is irradiated with an illuminating and image forming device and the light diffusely reflected from the dispersion is measured in a detector as to its color and/or brightness and indicated in an evaluating device.

14 Claims, 8 Drawing Sheets

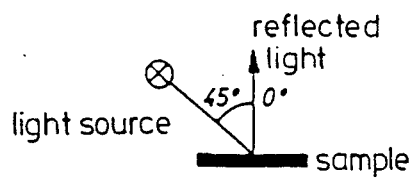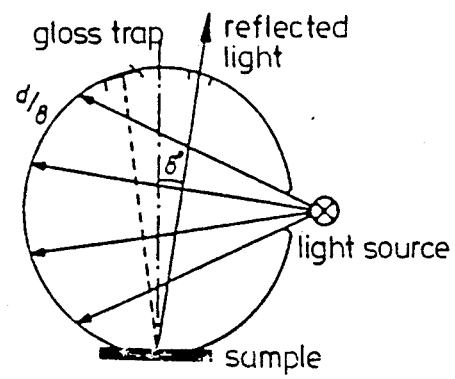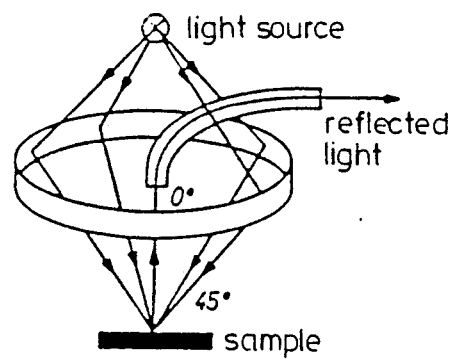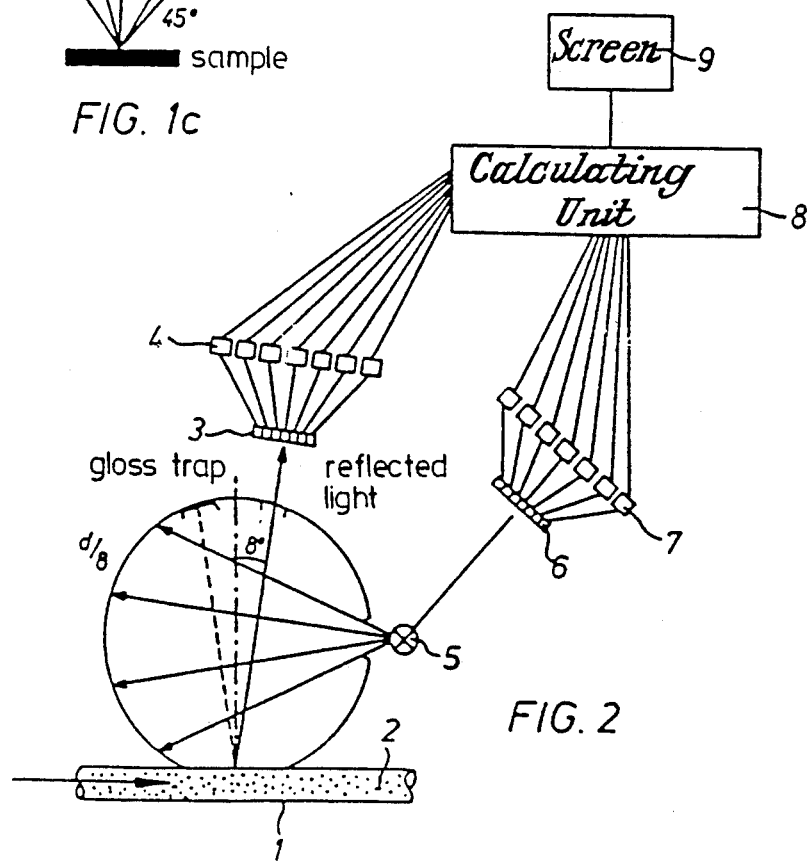

ARRANGEMENT FOR DETERMINING THE DEGREE OF DISPERSION OF MAGNETIC PIGMENTS IN A DISPERSION

This invention relates to an arrangement for determining the degree of dispersion of magnetic pigments in a dispersion according to the following explanation. In a polymeric solution of binder in which magnetic pigments and other additives are dispersed the magnetic pigments and the degree of dispersion is determined by means of an illuminating device and a detecting and evaluating device.

Dispersions containing magnetic pigments are used for the production of magnetic recording carriers such as magnetic discs and magnetic tapes. These dispersions consist of a pulverulent magnetic pigment, a solvent or solvent mixture, at least one organic polymer or prepolymer soluble or dispersible in this solvent (mixture), dispersing auxiliaries and other organic or inorganic additives such as slip agents, viscosity regulators, stabilizers and inorganic substances to regulate the conductivity, abrasion, roughness, etc. The dispersions are generally prepared by processes employed for the production of lacquers. In these processes it is very important not only to observe the chemical composition very accurately but also to employ a complicated mechanical process in dispersion apparatus which will be described below. This and the physical-chemical properties of the components of the dispersion and their interaction determine the internal structure of the dispersion, of which the degree of dispersion and the degree of agglomeration of the individual particles, in particular of the magnetic pigments, play a decisive role. Electrostatic and magnetostatic forces between the pigments may lead to the formation of agglomerates which only come to light later in the manufactured magnetic recording carrier.

The major characteristics which determine the quality of the dispersion are therefore the degree of dispersion or degree of agglomeration, the particle density and the viscosity. Another important factor is the stability of the dispersion, which depends to a large extent on the time in that it may change during the time that elapses between the preparation of the lacquer and casting of the dispersion. The dispersion is normally prepared in three stages:

1. Preliminary grinding of the magnetic pigment is carried out with or without solvent in the presence of a wetting agent and optionally a dissolved polymeric binder.

2. In the predispersion stage, the pigment deposit described under 1 is dispersed into a concentrated binder solution, whereupon other of the additives mentioned above may be added.

3. The required degree of dispersion of the magnetic dispersion is finally obtained in a more prolonged process of fine dispersion.

At the present time, the quality of the dispersion is tested during production by preparing a sample of cast dispersion which is substantially similar to a finished magnetic recording carrier, and its quality is then tested. Subsequent treatment of the dispersion depends on this test. It will be obvious that such testing is time consuming, expensive and inaccurate since it is not possible to have any information about the state of the dispersion immediately before and during application of the dispersion to a support.

EP No. 0 146 015 describes a rapid method for determining the degree of dispersion in flowing two-phase systems. The pressure drop in the dispersion as it flows along a specified length of path is measured. This method would appear to be too inaccurate for the purpose stated above.

A process for measuring the electrokinetic Zeta potential of a dispersion is disclosed in DE-PS No. 23 37 165. A sample stream is continuously removed from the dispersion under investigation and transferred to a separating cell in which the stream of sample is exposed to a magnetic field and divided up into several partial streams. These partial streams are then passed through separate measuring cells in which the solids content of the individual partial stream is determined. This method of measuring determines the electrostatic charge of the pigment in relation to the polymeric binder system and characterises the stability of the dispersion but not the degree of dispersion.

A process for determining the degree of dispersion of magnetic dispersions is known from Journal Dispersion Science and Technology, 7 (2), pages 159 to 185 (1986). This method uses the uptake of mercury on the surface of the magnetic pigments to assess their volume. This method is too elaborate and unsuitable as a rapid test.

According to EP No. 0 103 655, the dispersion flowing through a tube is exposed to a magnetic alternating field of variable frequency and the results are used to determine the susceptibility. This method of determination depends to a great extent on the coercivity of the magnetic pigments and on the rate of throughflow and is therefore unsuitable as a universal measuring method for use in production processes. A similar apparatus is described in Japanese Application No. 58-76758.

An apparatus for measuring the aggregation of particles against a wall or with one another is described in DE-OS No. 29 29 018. The particles are in this case dispersed in a stream of liquid or gas. The liquid or gaseous multiphase system is directed towards a transparent wall and illuminated. The light which is scattered, reflected or attenuated by absorption is directed towards a detector and assessed. Measurement of the aggregation of particles with one another or against the wall is only possible with highly diluted dispersions which are transparent. It is not suitable for highly concentrated dispersions containing magnetic particles, since such dispersions are opaque.

It was therefore an object of the present invention to provide a clear cut process and arrangement which would be suitable for determining the degree of dispersion of the magnetic pigments in a dispersion and would also be suitable as a basis for continuous measurement and monitoring of the relevant properties of the dispersion in the production process and would constitute a rapid and accurate method of determination.

This problem was solved according to the invention by an arrangement having the features mentioned above. Further details of the invention are contained in the sub-claims, the description and the drawings.

Figure 4:
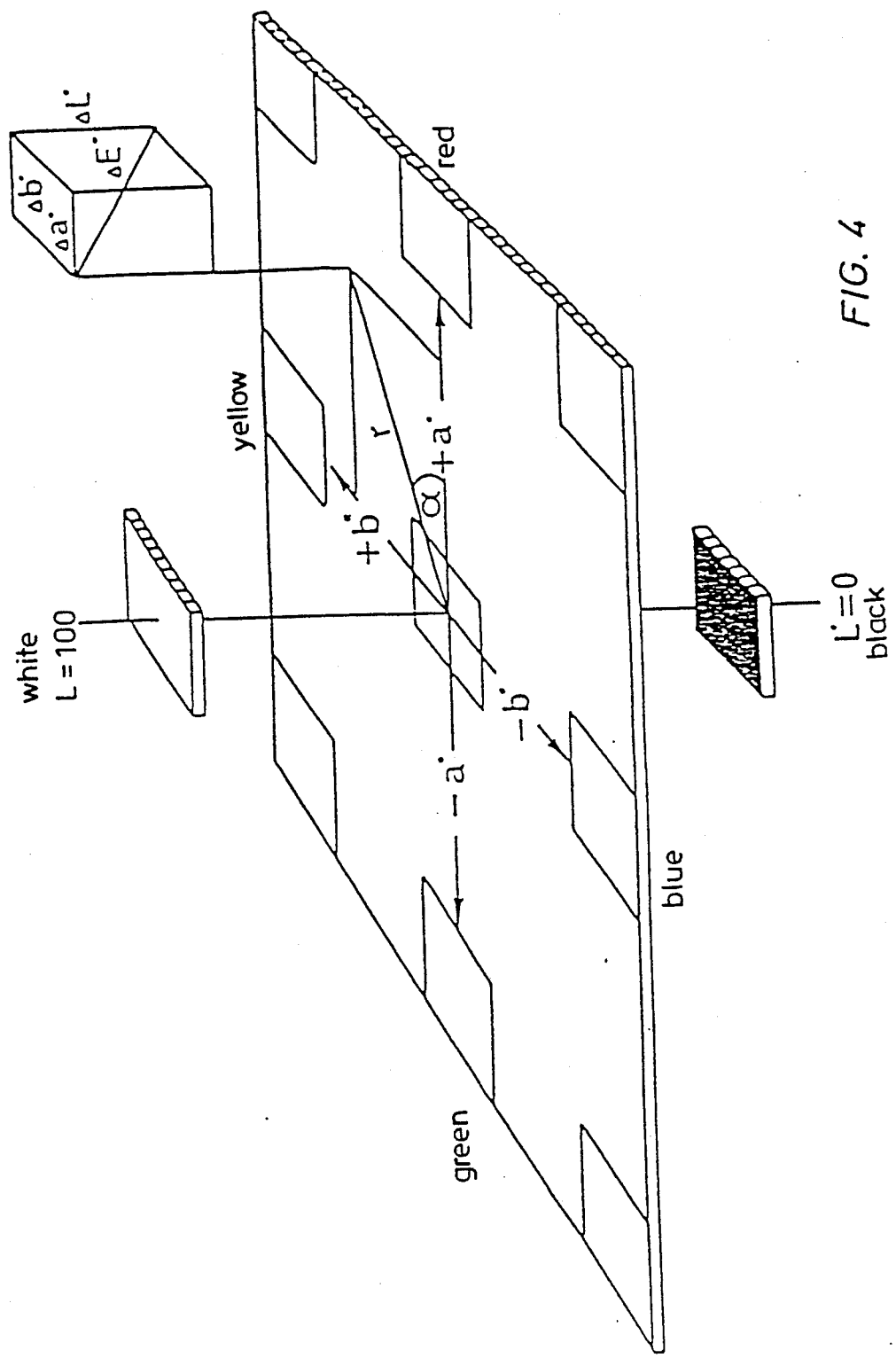
Figure 5:
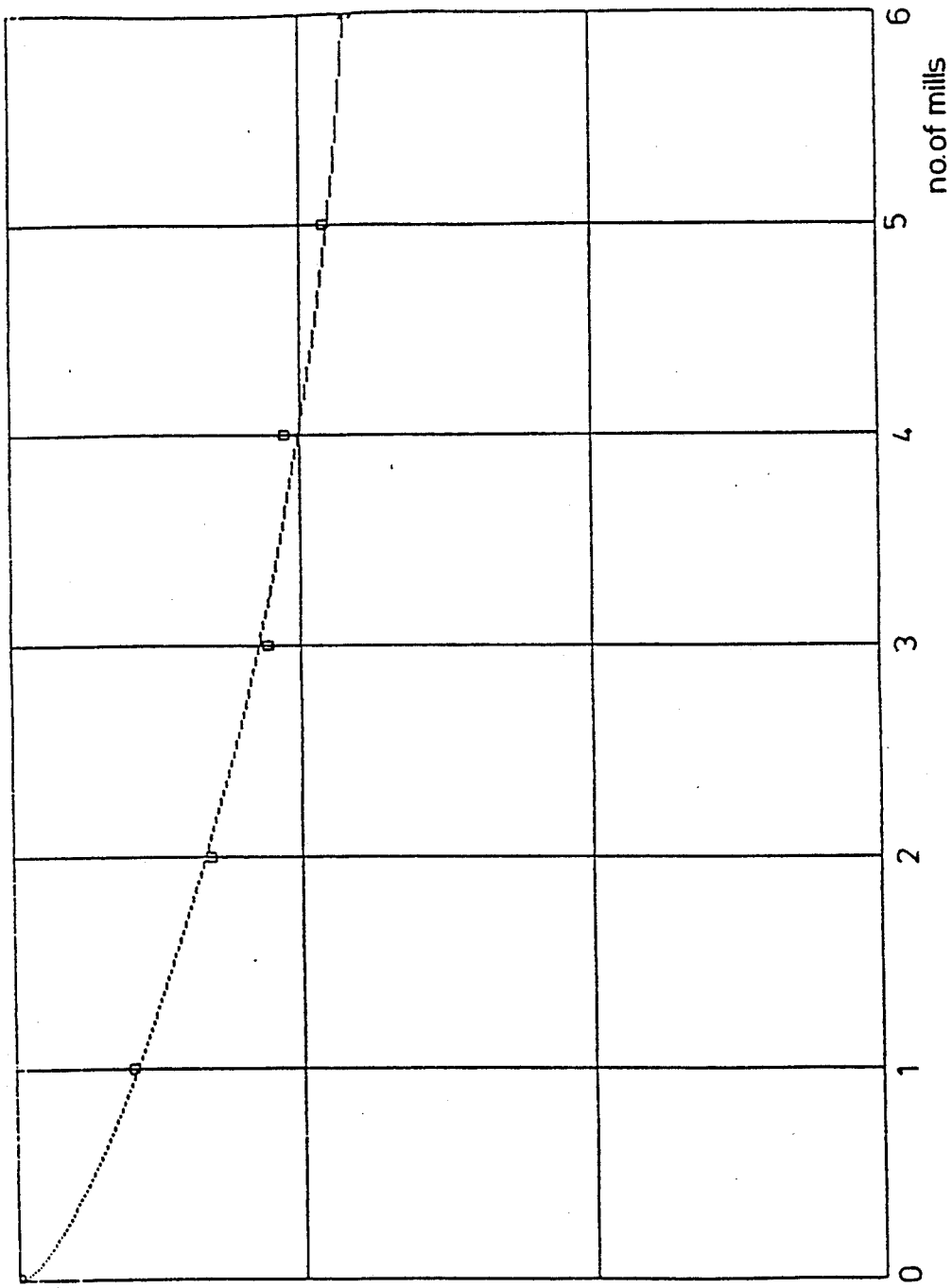
Figure 6:
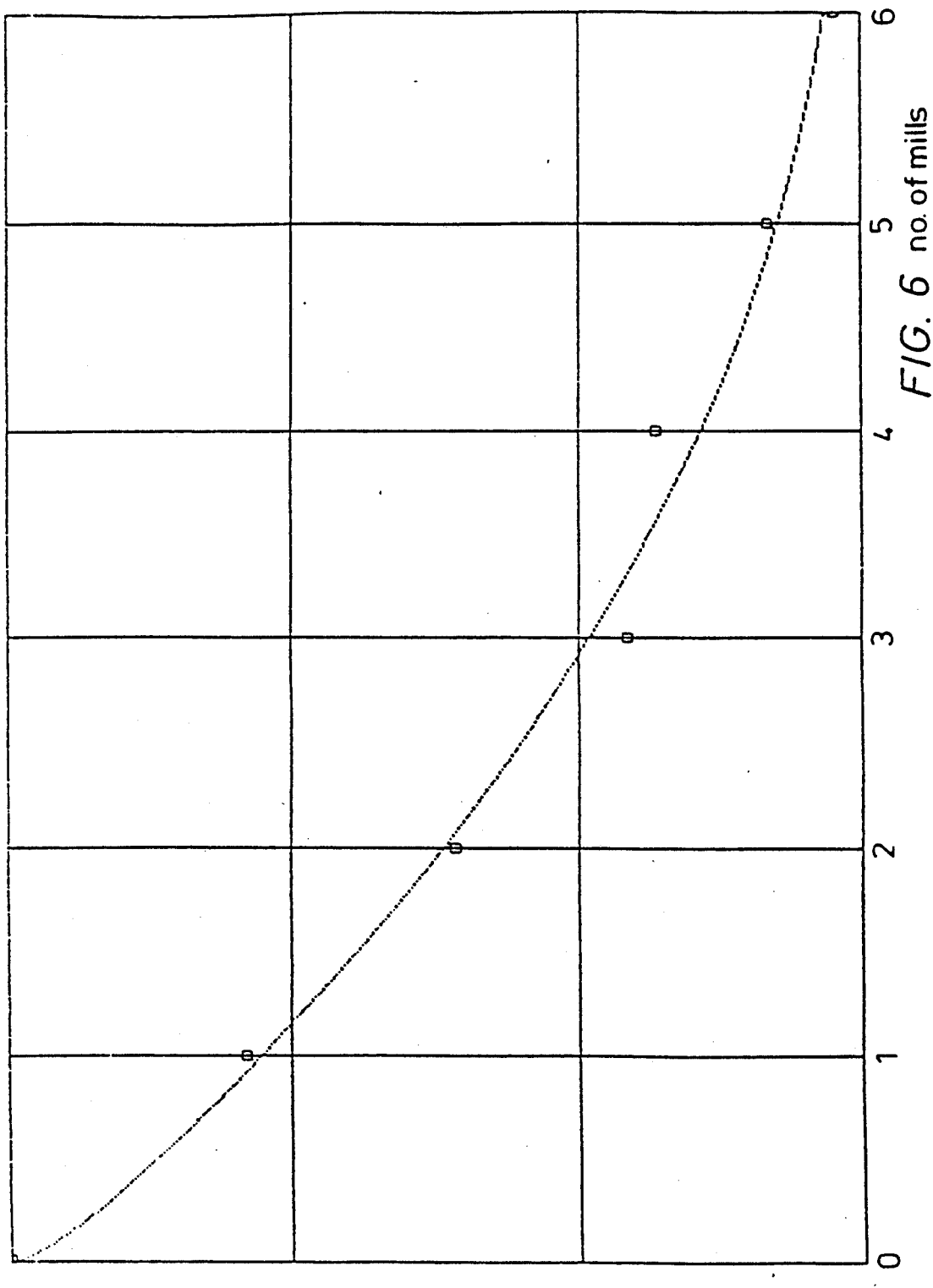
Figure 7:
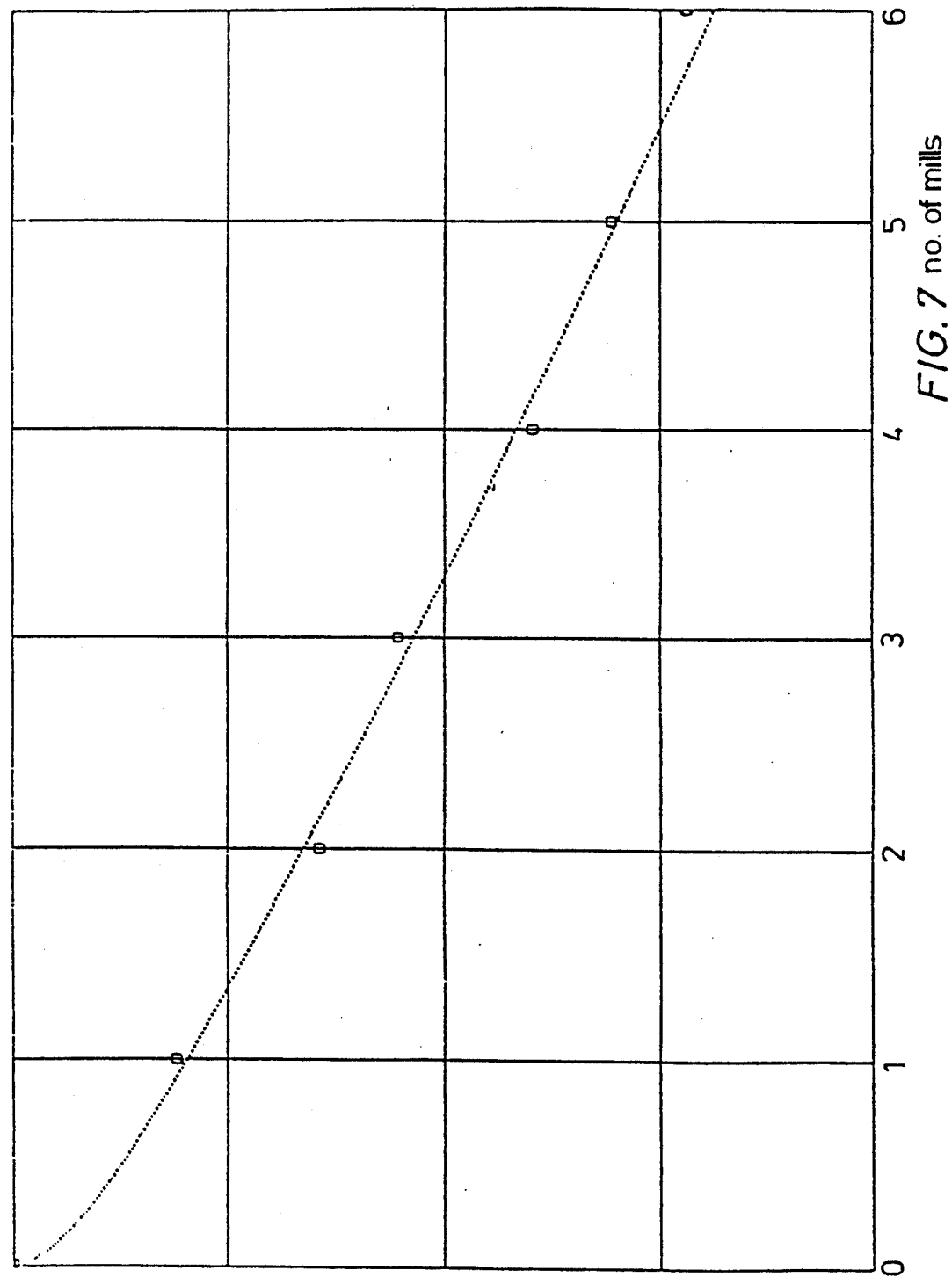
Figure 8:
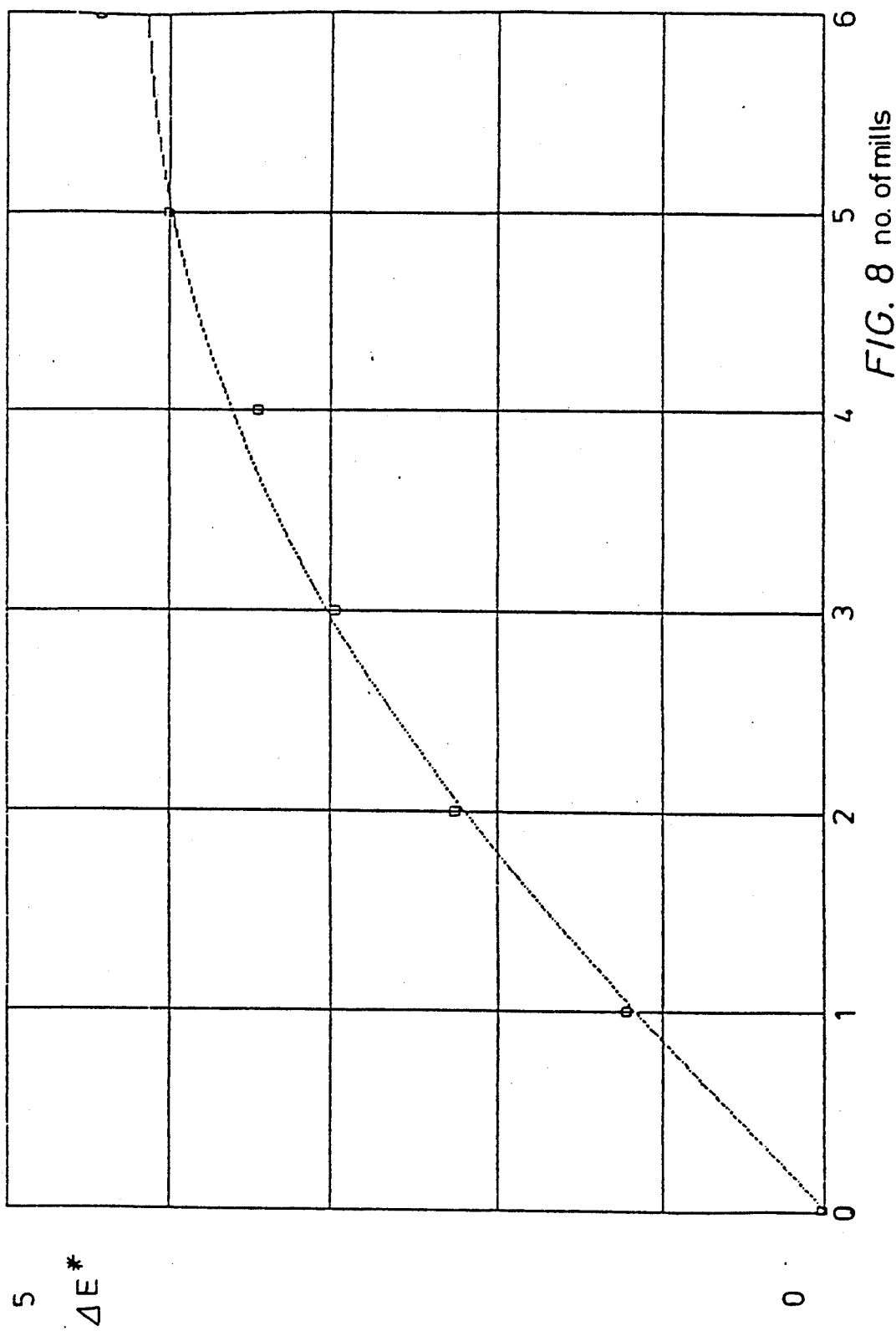

The invention will now be described in more detail with reference to the drawings, in which FIGS. 1a–c indicates schematically three different illumination and measurement geometries for determining the light reflected from the sample in accordance with the prior art, FIG. 2 illustrates schematically a preferred arrangement according to the invention for determining the degree of dispersion, FIG. 3 represents an exemplary embodiment of the method of measuring a sample with the arrangement according to the invention, FIG. 4 is a schematic representation of the CIE-LAB colour system and FIGS. 5–9 are graphic representations of the change in colour and/or brightness of dispersions measured in dependence upon the dispersing function, The invention essentially consists in that the dispersion is illuminated and the light diffusely reflected by the dispersion is assessed colorimetrically and compared with a standard. Colorimetric methods of determining a particular product quality are known, for example, from the technology of textile dyeing or the lacquering of articles in the case of solid substances. FIG. 1 shows three different conventional measuring geometries as laid down in CIE-Publication No. 15.

(a) The sample is exposed to light at an angle of incidence of 45° to the perpendicular and the quantity of light reflected at 0° is measured.

(b) The sample is illuminated diffusely through a hollow sphere which has an internal, matt white lining, and the light reflected at an angle of 8° to the perpendicular is measured. In this arrangement, a black gloss trap may be provided to eliminate the light due to gloss.

(c) The samples are illuminated all round at angles of 45° and the light reflected at 0° to the perpendicular is measured.

The method described under (b) was found to be the most suitable for the present purpose.

FIG. 2 is a schematic illustration of the arrangement according to the invention. The magnetic dispersion (2) flowing through a tube (1) which has transparent, as far as possible delustred walls is illuminated diffusely as described above. The diffusely reflected light is broken down spectrally, for example by means of a holographic grid (3), and the separated components of light are measured with the corresponding number of photoelectric diodes (4), for example at wavelength intervals of 20 nm in the region of 400 to 700 nm. The light emitted from the light source (5) is analogously broken down spectrally (6) and measured in the same way as the diffusely reflected light (7). An arrangement of two Xenon flash lamps operating under pulsed conditions in a two beam process are preferably employed. The method of colorimetric assessment is described below.

In the case described above, determination of the degree of dispersion is carried out continuously in a measuring station. If, however, several measuring stations are to be watched simultaneously, which may be necessary in the production process for the fine dispersion described above, each overflow tube from one dispersion apparatus to the next may be used as measuring station, in which case photoconductors which can be switched on according to the required time rhythm are used as central illuminating device and for measuring and assessment, as illustrated schematically in FIG. 3. Concrete embodiments of the arrangement according to the invention are given in the Examples.

The principle of colorimetric measurement consists, as is well known to the man of the art in this field, in measuring the light emitted from a sample by a spectral measurement carried out at certain wavelengths, the so-called selection wavelengths, inserting the measured values in colour physiological functions and calculating from the result the colour shade, colour saturation and brightness for a particular type of standard light. The CIE-LAB colour system according to CIE-Publication No. 15 has become widely established as a method of presenting the calculated values. In this system, the colour values ($\Delta a^*$, $\Delta b^*$) and the brightness values ($\Delta L^*$) are represented as vectors extending from the achromatic point at the centre of the diagram to make up the end value, the colour distance $\Delta E^*$.

$$\Delta E^* = \sqrt{(\Delta L^*)^2 + (\Delta a^*)^2 + (\Delta b^*)^2}$$

In the present case, the light which is emitted from the light source (5) and from the sample of dispersion (2) and is decomposed spectrally (3, 6) and measured by the photoelectric diodes (4, 7) is processed in the calculating unit 8 (FIG. 2) and used to calculated the colour distance $\Delta E^*$, i.e. the colour and/or brightness distance between the light source (reference) and the light diffusely reflected from the sample, and the result is indicated, for example digitally, or displayed graphically on a screen (9). Apparatus of this type are available commercially and have measuring and calculating times of less than 1 second so that the required values are available extremely rapidly.

It is found, as will be seen from the following Examples, that the changes in colour and/or brightness during coarse dispersion and fine dispersion give an extremely sensitive indication of the degree of dispersion of the magnetic pigments, which is much more accurate than previous measuring methods mentioned above so that the aim of accurate quality control of the dispersion can be achieved. The desired end value is obtained when the colour distance is equal to that which has been laid down on the basis of a colorimetric measurement obtained with a reference sample (standard).

EXAMPLE 1 (ALL FIGURES ARE PARTS BY WEIGHT)

Needle-shaped cobalt doped $\gamma$-$Fe_2O_3$ having a coercive field strength of 27 kA/m and a saturation magnetization of 1.5 T was predispersed in batches of 1200 parts with 105 parts of a vinyl chloride/vinyl acetate/vinyl alcohol copolymer, 128 parts of a polyester polyurethane, 30 parts of acid alkyl phosphate as dispersing agent, 3 parts of fatty acid and 12 parts of zinc oleate in 2250 parts of a solvent mixture of tetrahydrofuran/cyclohexanone in a vessel with turbo mixer for 5 hours. The resulting dispersion was pumped into a transfer vessel with slowly rotating blade stirrers from which the dispersion was continuously pumped through a series of six successive ball mills with stirrers for fine dispersion. Each of these mills had a capacity of 125 l and contained 91 l of aluminium oxide grinding balls 1 to 1.5 mm in diameter. The residence time of the dispersion in each mill was 30 minutes. Measuring stations for the arrangement according to the invention were provided at the entrance to the first mill (measuring station 0) and at the exit from each mill (measuring stations 1 to 6) and both the measuring light and diffusely deflected light were transmitted through photoconductors 4.5 m in length. The dispersion discharged from the last mill of the cascade was filtered under pressure through a filter with a pore size of 1 $\mu$m. 0.85 Parts of cross-linking agent (Desmodur L TM of Bayer AG) dissolved in 1 part of tetrahydrofuran as solvent was added per 100 parts of dispersion and the dispersion was applied to a polyethylene terephthalate film 16 $\mu$m in thickness by means of an extrusion caster to form on this film a layer with a dry thickness of 3 $\mu$m, the magnetic pigments being at the same time orientated by means of a permanent magnet. The dry layer was smoothed by passing it between two heated rollers under pressure.

The assessment at the individual measuring stations produced the results shown in the graphs of FIGS. 5 to 8, in which the values for Δa*, Δb*, ΔL* and ΔE* are entered against the individual measuring stations. The measuring value for station 0 was arbitrarily set at 0. The results obtained depend on the degree of dispersion to a greater or less extent, depending on the type of measured value. The shape of the graph may be represented mathematically by the calculating unit as a result of a regression calculation based on a polynomium of the nth degree or a logarithmic function.

The results showed excellent electroacoustic and mechanical data of the magnetic recording carrier prepared as described above whereas samples which had passed only through 1 to 5 mills were inferior in their properties.

EXAMPLE 2

A dispersion analogous to that of Example 1 was prepared but with 1200 parts of needle-shaped cobalt doped γ-$Fe_2O_3$ having a coercive field strength of 61.4 kA/m. After 5 hours of predispersion, the dispersion was introduced into a vessel having a capacity of 700 ml and from this vessel the dispersion was transferred in a continuous circulation through a funnel into a laboratory ball mill with stirrer which had a volumetric capacity of 250 ml and contained 225 ml of steel balls. A sample was removed after every 10 minutes and 20 minutes of grinding, cross-linking agent was added as described in Example 1, and the sample was cast and dried. At each measuring station, three samples were placed above one another for colour measurement to simulate a layer of infinite thickness. The samples were also measured electroacoustically in the usual manner.

TABLE 1

| Grinding time (min) | ΔL* | Δb* | IHC (kA/m) | Br/Bs |
| --- | --- | --- | --- | --- |
| 0 | 42.75 | 11.67 | 61.4 | 0.78 |
| 10 | 40.80 | 11.06 | 61.6 | 0.81 |
| 20 | 40.06 | 10.41 | 61.7 | 0.81 |
| 40 | 39.03 | 9.80 | 61.0 | 0.80 |

Table 1 shows the colorimetric and electroacoustic values obtained from the cast samples. The Table shows that the colorimetric determination gives a much more accurate figure for the degree of dispersion of the magentic pigment than the measurement with electroacoustic data which, moreover, is more time consuming.

EXAMPLE 3

737 Parts of needle-shaped $CrO_2$ having a coercive force of 39.8 kA/m were dispersed together with 25 parts of vinylidene chloride/acrylonitrile copolymer, 23 parts of lecithin, 580 parts of tetrahydrofuran and 209 parts of cyclohexanone as solvent and added to a binder solution consisting of 27 parts of vinylidene chloride/acrylonitrile copolymer, 106 parts of polyester urethane in 534 parts of tetrahydrofuran and 200 parts of cyclohexanone. The dispersion batch obtained was predispersed in a vessel with turbo mixer for 6 hours, pumped into an intermediate vessel, and pumped from this vessel continuously through a succession of 7 ball mills with stirrers for fine dispersion: Each of these ball mills had a volumetric capacity of 125 l and was filled to an extent of 80% with ceramic grinding bodies 1 to 1.5 mm in diameter. The residence time in each mill was 25 minutes. The finely divided dispersion was then pressed through a filter with a pore width of 1 μm and mixed with 4 parts of fatty acid, 9 parts of butyl stearate, 15 parts of a 75% solution in ethyl acetate of a cross-linking agent (Desmodur L of Bayer AG) and 0.2 parts of iron acetyl acetonate and the mixture was introduced into an extrusion caster from which it was applied to a PET film 8 μm in thickness to form on this film a layer with a dry thickness of 3 μm, and the layer was oriented in the magnetic field, dried and calendered.

Figure 9:
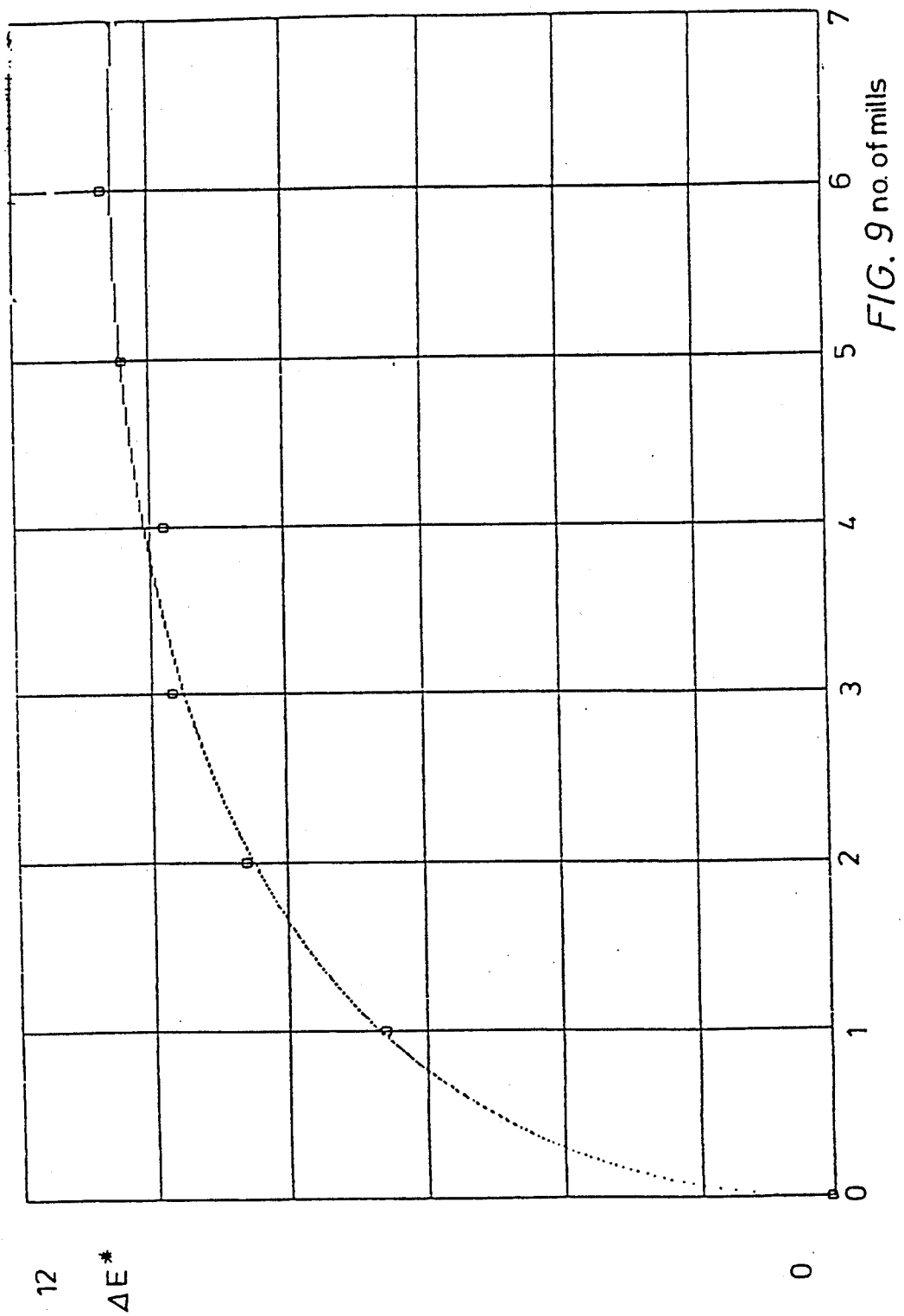

Measurement of the degree of dispersion by means of the apparatus according to the invention and the concomitant removal of samples of dispersion were carried out as in Example 1. FIG. 9 shows the graph of the ΔE* as a measure of the degree of dispersion in the seven mills. The value measured at the entrance to the first mill was again set at 0.

EXAMPLE 4

A dispersion having the same composition as in Example 3 was prepared and after predispersion it was finely dispersed in a ball mill with stirrer as in Example 2. Samples were taken at regular intervals, cast and dried and examined colorimetrically and electroacoustically. The results obtained are entered in Table 2.

TABLE 2

| Grinding time (min) | ΔL* | Δb* | IHC kA/m | Br/Bs |
| --- | --- | --- | --- | --- |
| 0 | 29.52 | −2.47 | 60.8 | 0.80 |
| 10 | 24.50 | −4.22 | 60.6 | 0.83 |
| 20 | 23.14 | −4.65 | 60.5 | 0.84 |
| 30 | 22.33 | −4.86 | 60.5 | 0.84 |
| 40 | 22.19 | −4.95 | 60.4 | 0.84 |
| 60 | 21.96 | −4.93 | 60.2 | 0.84 |

The colour measurement is again found to determine the correct degree of dispersion much more accurately and more rapidly. Similar results were obtained when metal powders or ferrites were used as magnetic pigments. The colorimetric determination of the degree of dispersion was in all cases considerably more accurate than the previously known methods. *

* Of course also mixtures of different sorts of magnetic pigments in a dispersion may be evaluated in the inventive arrangement.

The advantages of the apparatus according to the invention may be summarized as follows:

Rapid and accurate determination of the degree of dispersion of the magnetic pigments in dispersions in a liquid state or cast samples in the dry state.

Continuous monitoring of the degree of dispersion during predispersion and fine dispersion in continuously operating manufacturing plants.

Faults in the dispersion apparatus or in the cascade of mills can be immediately detected, localized and suitably counteracted so that no loss of production occurs.

The process of determining the degree of dispersion can to a large extent be automated so that very little monitoring work is required.

I claim:

1. A method for determining the degree of dispersion of magnetic pigments in a dispersion in an illuminating and measurement apparatus
    comprising the sequential steps of
    providing a pulverulent magnetic pigment, a solvent and at least one polymer soluble in the solvent in a dispersion, passing the dispersion through a conduit having at least a section transparent to radiation in the visible spectrum, providing light in the visible spectrum from an illuminating means, diffusely reflecting a portion of said light from said dispersion as it passes through said transparent section, directing said diffusely reflected light to a first holographic grid, breaking down said diffusely reflected light spectrally at said first grid, directing another portion of the light as a reference light from said illuminating means directly to a second holographic grid and breaking down said reference light spectrally at said second grid, measuring the spectrally broken down light from said first and second grids at photoelectric means for measuring visible radiation, observing the color and brightness of the light spectrally broken down at the grids and measured at the photoelectric means providing a calculating unit with data from observations at the photoelectric means, performing in the calculating unit calculations from the data obtained from the photoelectric means, the equation for determining the color distance in a color system of the diffusely reflected light which is $$\Delta E^* = \sqrt{(\Delta L^*)^2 + (\Delta a^*)^2 + (\Delta b^*)^2}$$

in which

L* represents the range of brightness from white to dark,

Δa* represents the range of color values from red to green,

Δb* represents the range of color values from yellow to blue,

The color and brightness values being determined from the achromatic center point of the color system, ΔE* represents the color and/or brightness distance between the reference light and diffusely reflected light and performing in the calculating unit calculation from the obtained data to obtain the degree of dispersion of the magnetic pigment.

2. A method for determining the degree of dispersion of magnetic pigments in a dispersion in an illuminating and measuring apparatus comprising the sequential steps of providing a pulverulent magnetic pigment, a solvent and at least one polymer soluble in the solvent in a dispersion, casting the dispersion in a layer on a transparent layer support and transporting said cast layer on said support providing light in the visible spectrum from an illuminating means, diffusely reflecting a portion of said light from said dispersion as it is transported on said transparent layer support directing said diffusely reflected light to a first holographic grid, breaking down said diffusely reflected light spectrally at said first grid, directing another portion of the light as a reference light from said illuminating means directly to a second holographic grid, and breaking down said reference light spectrally at said second grid, measuring the spectrally broken down light from said first and second grids at photoelectric means for measuring visible radiation, observing the color and brightness of the light spectrally broken down at the grids and measured at the photoelectric means providing a calculating unit with data from observations at the photoelectric means, performing in the calculating unit calculations from the data obtained from the photoelectric means, the equation for determining the color distance in a color system of the diffusely reflected light which is $$\Delta E^* = \sqrt{(\Delta L^*)^2 + (\Delta a^*)^2 + (\Delta b^*)^2}$$

in which

ΔL* represents the range of brightness from white to dark,

Δa* represents the range of color values from red to green,

Δb* represents the range of color values from yellow to blue, the color and brightness values being determined from the achromatic center point of the color system, ΔE* represents the color and/or brightness distance between the reference light and diffusely reflected light and performing in the calculating unit calculations from the obtained data to obtain the degree of dispersion of the magnetic pigment.

3. In the method of claim 2 the steps of casting several layers of dispersion on the transparent support.

4. An illuminating and measuring apparatus for determining the degree of dispersion of magnetic pigments in a dispersion comprising in combination in a production of magnetic recording carriers a dispersion means for providing a dispersion of pulverulent magnetic pigment in a solvent and at least one polymer soluble in the solvent a transparent conduit for passing dispersion, an illuminating means providing light in the visible spectrum means for diffusely reflecting a portion of said light off of said dispersion as it passes in said transparent conduit a first holographic grid for receiving said diffusely reflecting light whereby said light is broken down spectrally to form a spectra from said light.

a second holographic grid for receiving a reference light directly from said illuminating means whereby said reference light is broken down spectrally to form spectra, photoelectric means for measuring said spectra of said reflected light and said reference light and providing data correlated to said spectra, a calculating unit receiving data in signals representing color and brightness values from said photoelectric means, means for processing said signals to evaluate the degree of dispersion of the processed dispersion passing through the transparent conduit and means for performing in the calculating unit from the data in the signals calculations in accordance with the equation for determining the color distance in a color system of the diffusely reflected light which is $$\Delta E^* = \sqrt{(\Delta L^*)^2 + (\Delta a^*)^2 + (\Delta b^*)^2}$$

in which $\Delta L^*$ represents the range of brightness from white to dark $\Delta a^*$ represents the range of color values from red to green, $\Delta b^*$ represents the range of color values from yellow to blue, the color and brightness values being determined from the achromatic center point of the color system, $\Delta E^*$ represents the color and/or brightness distance between the reference light and diffusely reflected light and means in the calculating unit for performing calculations for providing the color distance and color and brightness values as a measure of the degree of dispersion.

5. The apparatus as claimed in claim 4 having means for continuously passing the dispersion through the conduit whereby the degree of dispersion is continuously measured.

6. An illuminating and measuring apparatus for determining the degree of dispersion of magnetic pigments in a dispersion comprising in combination in a production of magnetic recording carriers a dispersion means for providing a dispersion of pulverulent magnetic pigment in a solvent and at least one polymer soluble in the solvent a layer of said dispersion of magnetic pigments on a transparent layer support, an illuminating means providing light in the visible spectrum, means for diffusely reflecting a position of said light off of said dispersion in said supported layer, a first holographic grid for receiving said diffusely reflecting light whereby said light is broken down spectrally to form spectra from said light.

a second holographic grid for receiving a reference light directly from said illuminating means whereby said reference light is broken down spectrally to form spectra, photoelectric means for measuring said spectra of said reflected light and said reference light and providing data correlated to said spectra, a calculating unit receiving data in signals representing color and brightness values from said photoelectric means, means for processing said signals to evaluate the degree of dispersion of the processed dispersion passing through the transparent conduit and means for performing in the calculating unit from the data in the signals calculations in accordance with the equation for determining the color distance in a color system of the diffusely reflected light which is $$\Delta E^* = \sqrt{(\Delta L^*)^2 + (\Delta a^*)^2 + (\Delta b^*)^2}$$

in which $\Delta L^*$ represents the range of brightness from white to dark, $\Delta a^*$ represents the range of color values from red to green, $\Delta b^*$ represents the range of color values from yellow to blue, the color and brightness values being determined from the achromatic center point of the color system, $\Delta E^*$ represents the color and/or brightness distance between the reference light and diffusely reflected light and means in the calculating unit for performing calculations for providing the color distance and color and brightness values as a measure of the degree of dispersion.

7. An illuminating and measuring apparatus as claimed in claim 6 having in the combination several layers of dispersions of magnetic pigment on the transparent support.

8. The method as claimed in claim 1, 2 or 3 wherein the illuminating means is two pulsed Xenon lamps.

9. In the method as claimed in claim 1, 2 or 3 measuring and evaluating the degree of dispersion in a plurality of dispersions.

10. In the method of claim 9 simultaneously measuring and evaluating the degree of dispersion in said plurality of dispersions.

11. In the apparatus of claim 7 means for simultaneously determining the degree of dispersion in said plurality of dispersions.

12. The method as claimed in claim 2 or 3 wherein the dispersion is continuously transported on the support and the degree of dispersion is continuously measured.

13. The apparatus as claimed in claims 4, 6 or 7 wherein the illuminating means is two pulsed Xenon lamps.

14. Apparatus as claimed in claims 4, 6 or 7 comprising in combination a plurality of illuminating and measuring means for determining the degree of dispersion in a plurality of dispersions.

* * * * *